US006357491B1

(12) United States Patent
Buchanan et al.

(10) Patent No.: US 6,357,491 B1
(45) Date of Patent: Mar. 19, 2002

(54) CONTROLLING THE MISUSE OF AN OPERATING-ROOM APPARATUS

(75) Inventors: Richard W. Buchanan, Hamburg; Keith Martin, Orchard Park, both of NY (US)

(73) Assignee: Gaymar Industries Inc., Orchard Park, NY (US)

( * ) Notice: Subject to any disclaimer, the term of this patent is extended or adjusted under 35 U.S.C. 154(b) by 0 days.

(21) Appl. No.: 09/349,537

(22) Filed: Jul. 8, 1999

(51) Int. Cl.[7] ............................ B65B 31/00; B67C 3/00

(52) U.S. Cl. ............................... 141/4; 141/39; 141/47; 141/67; 141/83; 141/95; 141/114; 141/197; 141/313; 607/107; 5/423

(58) Field of Search ................................ 141/4, 10, 37, 141/39, 47, 67, 83, 94, 95, 114, 192, 197, 313, 392; 607/104, 107; 5/423

(56) References Cited

U.S. PATENT DOCUMENTS 5,300,098 A * 4/1994 Philipot ....................... 607/96
6,126,681 A 10/2000 Van Duren et al. ........... 607/96
6,143,020 A * 11/2000 Shigezawa et al. ........... 607/96
6,146,412 A * 11/2000 Van Duren ................. 607/107

* cited by examiner

*Primary Examiner*—Timothy L. Maust
(74) *Attorney, Agent, or Firm*—Nixon Peabody LLP

(57) ABSTRACT

A device designed to interconnect with an inflatable thermia blanket. The device conveys a medium into the blanket, which applies an internal pressure to the device, and has at least two temperature settings for controlling the temperature of the medium and a pressure sensing apparatus. The pressure sensing apparatus measures the internal pressure. And when the measurement exceeds a predetermined level of internal pressure then any one of the at least two temperature settings is useable. Otherwise, when the measurement does not exceed the predetermined level of internal pressure, the device will either convey the medium at a predetermined temperature setting, which can include shutting the device down.

16 Claims, 7 Drawing Sheets

10
22
18a
18b
18c
20
16
14
12

10
12
14
16
18a
18b
18c
20
22

CONTROLLING THE MISUSE OF AN OPERATING-ROOM APPARATUS

FIELD OF THE INVENTION

The present invention relates to a device intended to convey a medium to a blanket, in particular a hypothermia blanket, a hyperthermia blanket, or a hypo/hyperthermia blanket.

BACKGROUND OF THE INVENTION

Hypothermia blankets, hyperthermia blankets, and hypo/hyperthermia blankets are designed to direct a medium having a predetermined temperature to a patient. The medium is supplied to the blankets from a conventional pump, blower, or other conventional devices for conveying such a medium, i.e., air, through a conduit, like a flexible hose.

The devices normally have multiple temperature settings. The operating personnel selects one of the temperature settings to provide the desired temperature for the patient. In some instances, nurses and other operating room sometimes elect to warm themselves by disengaging the hose from the blanket.

When this misuse occurs the operating personnel may burn and/or damage their skin or body hair if the temperature of the medium is to high. Even though this use of the device is unacceptable, the inventors have modified the device to reduce the chances that personnel can injure themselves.

Another misuse includes cutting the blanket itself. The blanket has a particular pattern to ensure the medium is dispersed upon the patient in a safe and desired pattern. In some instances, the operating-room personnel cuts, and sometimes attempts to repair, the blanket which can alter the desired and safe distribution of the medium to the patient. When the blanket's distribution system is altered, the patient's skin or body hairs may be burned and/or damaged if the temperature of the medium is to high.

Another problem occurs when the hospital purchased the device and does not use the hypothermia blankets, hyperthermia blankets, and hypo/hyperthermia blankets. The operating personnel have inserted the hose of the device under a conventional operating room blanket. This misuse can damage and/or burn the skin or body hairs of the patient because a conventional operating room blanket does not safely distribute the medium to the patient. Accordingly, this problem must be resolved.

The present invention solves these problems.

SUMMARY OF THE INVENTION

The present invention details a device designed to interconnect with an inflatable thermia blanket. The device conveys a medium into the blanket, which applies an internal pressure to the device, and has at least two temperature settings for controlling the temperature of the medium and a pressure sensing apparatus. The pressure sensing apparatus measures the internal pressure. And when the measurement exceeds a predetermined level of internal pressure then any one of the at least two temperature settings is usable. Otherwise, when the measurement does not exceed the predetermined level of internal pressure, the device will either convey the medium at a predetermined temperature setting, which can include shutting the device down.

The above and other objects, features, and advantages of the present invention will be apparent in the following detailed description of the preferred embodiments thereof taken in conjunction with the accompanying drawings wherein the same reference numerals denote the same or similar parts throughout the several views.

DETAILED DESCRIPTION OF THE INVENTION

Figure 1:
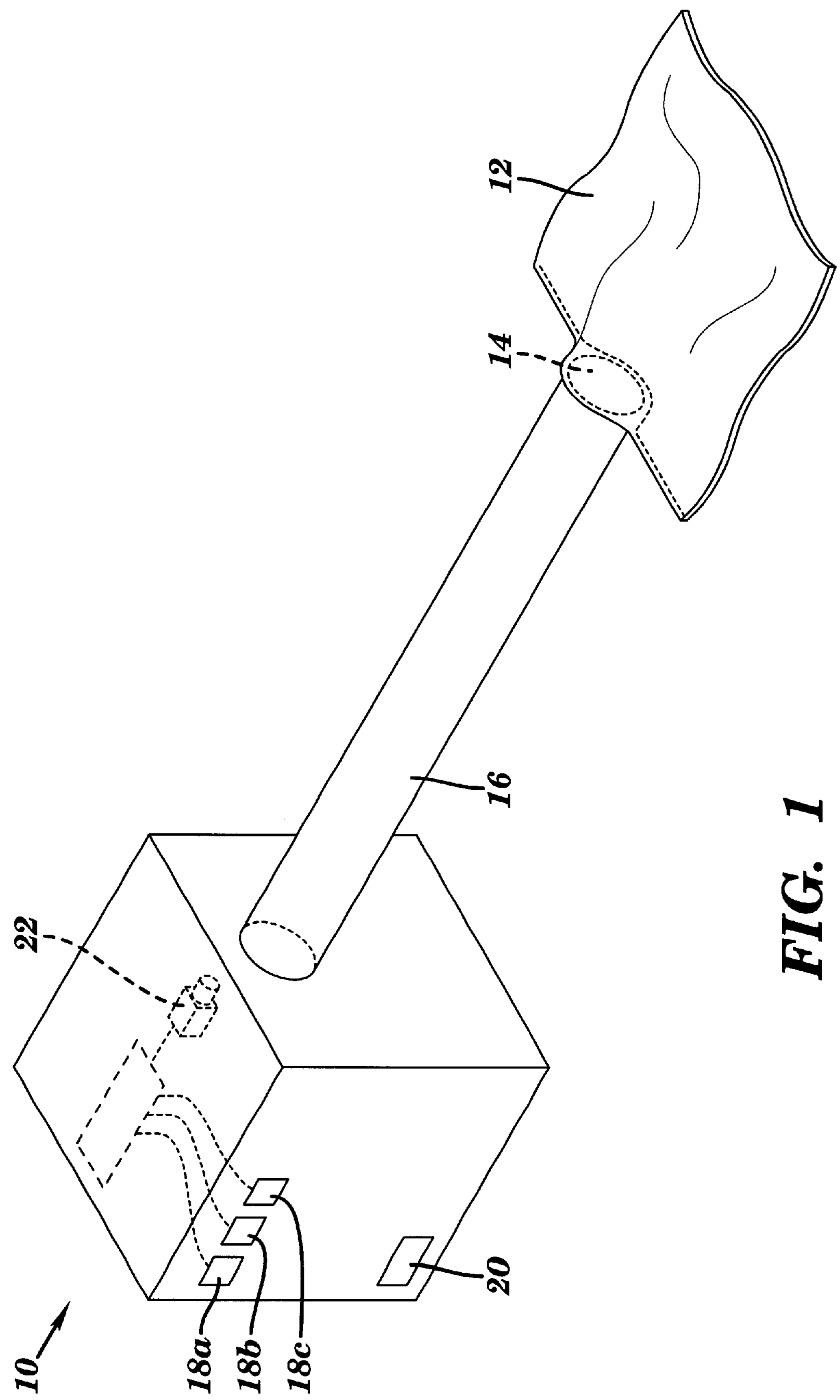
FIG. 1 is a view illustrating the present invention.

Referring to FIG. 1, the present invention details a conventional device 10, i.e., THERMACARE® blowers by Gaymar Industries, Inc. of Orchard Park, N.Y., which is designed to interconnect with an inflatable thermia blanket 12 and to convey a medium into the blanket 12. The blanket 12 is any conventional hypothermia blanket, hyperthermia blanket, or hypo/hyperthermia blanket, such as the THERMACARE® blankets by Gaymar Industries, Inc. of Orchard Park, N.Y. This blanket 12 has an aperture 14 to receive a first conduit 16 from the device 10.

In many conventional devices 10, the devices 10 have numerous temperature switches 18 (*a,b,c*), and at least one on/off switch 20. These switches 18(*a,b,c*), 20 are conventional switches. Examples of conventional switches include touch pads and throw-switches, which are conventional light switches.

Turning to the temperature switches 18, device 10 is designed so only one temperature switch 18 can be operable at one time. Accordingly, when a user presses one switch 18*a*, all other switches 18*b*, 18*c* are deactivated. Likewise when switch 18*b* is activated, the switch 18*a* is deactivated and switch 18*c* remains deactivated.

Each temperature switch 18*a*, 18*b*, 18*c* activates the device 10 to heat, cool, and/or convey a medium having a distinct and desired temperature setting to the blanket 12. Examples of a distinct temperature include, and are not limited to, 50° F., room temperature, 90° F., 100° F., and 110° F.

Obviously, the medium is a material which can be conveyed from the device 10 to the blanket 12, the blanket 12 then distributes the medium to a patient, and the medium be at the desired temperature setting. Examples of this medium include gases such as atmospheric air, and liquids such as water. Preferably, the medium is atmospheric air.

The first conduit 16 directs the medium from the device 10 to the blanket 12. Moreover, the first conduit 16 can be made of any conventional tubing material. Examples of such material include polymeric, metal, wood, or paper. Accordingly, the first conduit 16 can be flexible, rigid, disposable, and/or permanent. In any embodiment, the first conduit 16 must transport the medium at the desired temperature.

The blanket 12 receives the medium and therefore inflates. Under normal operating proceedings, for example when the blanket 12 is not cut or poorly repaired from a cut, the medium within the blanket 12, the first conduit 16, and the device 10, and within a predetermined time period has an internal pressure that exceeds a predetermined level of internal pressure.

Figure 2:
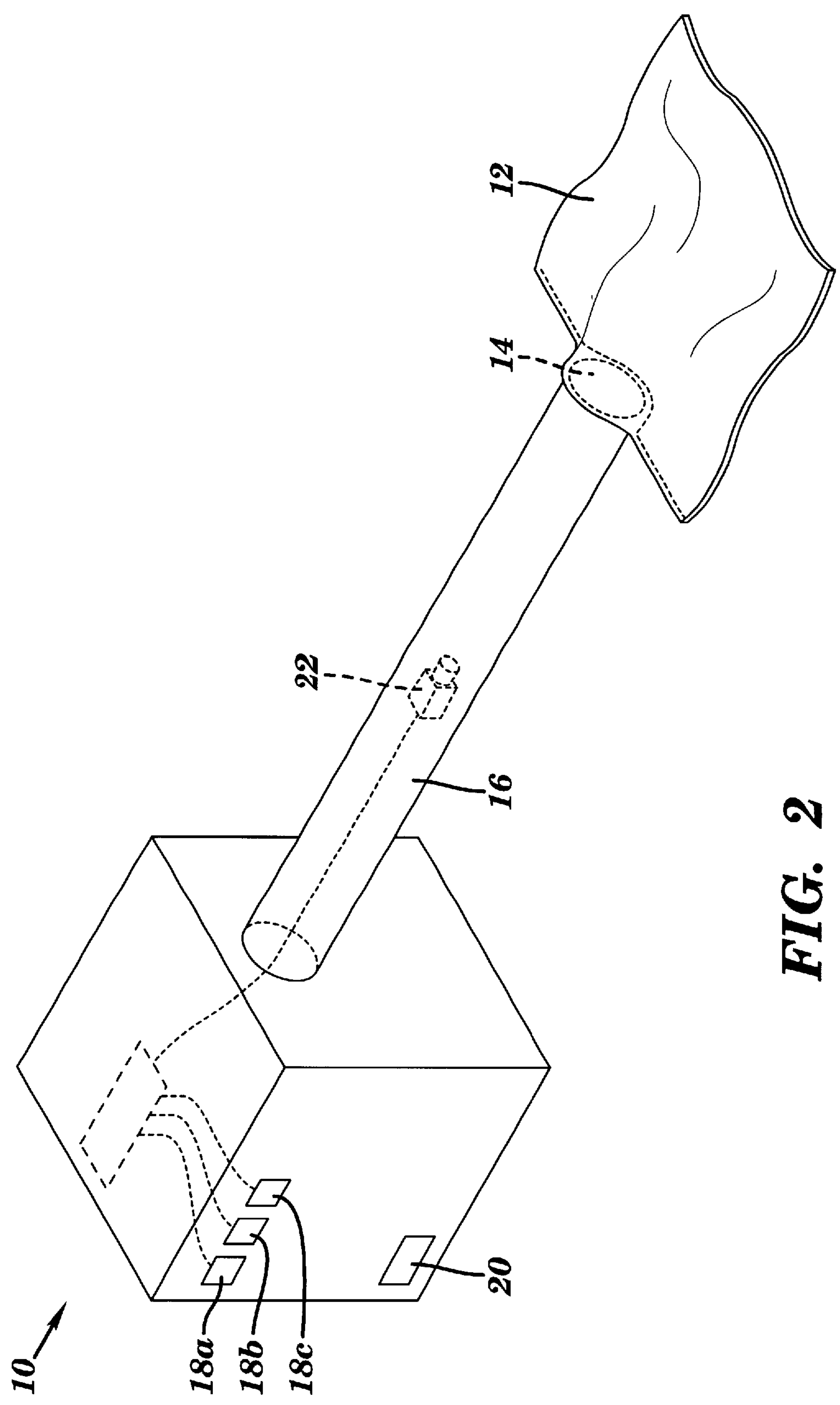
FIGS. 2–7 are alternative embodiments of FIG. 1.
Figure 3:
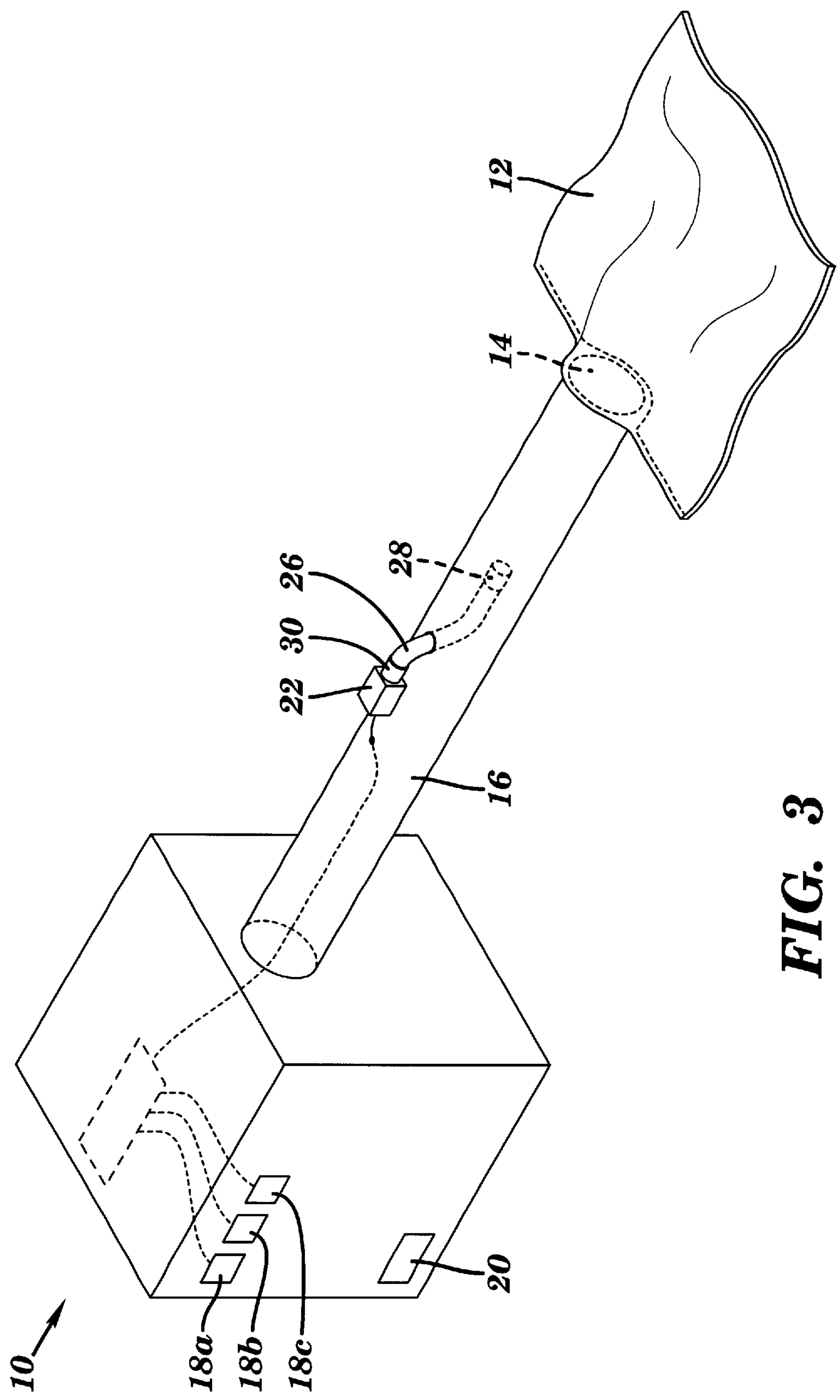
Figure 4:
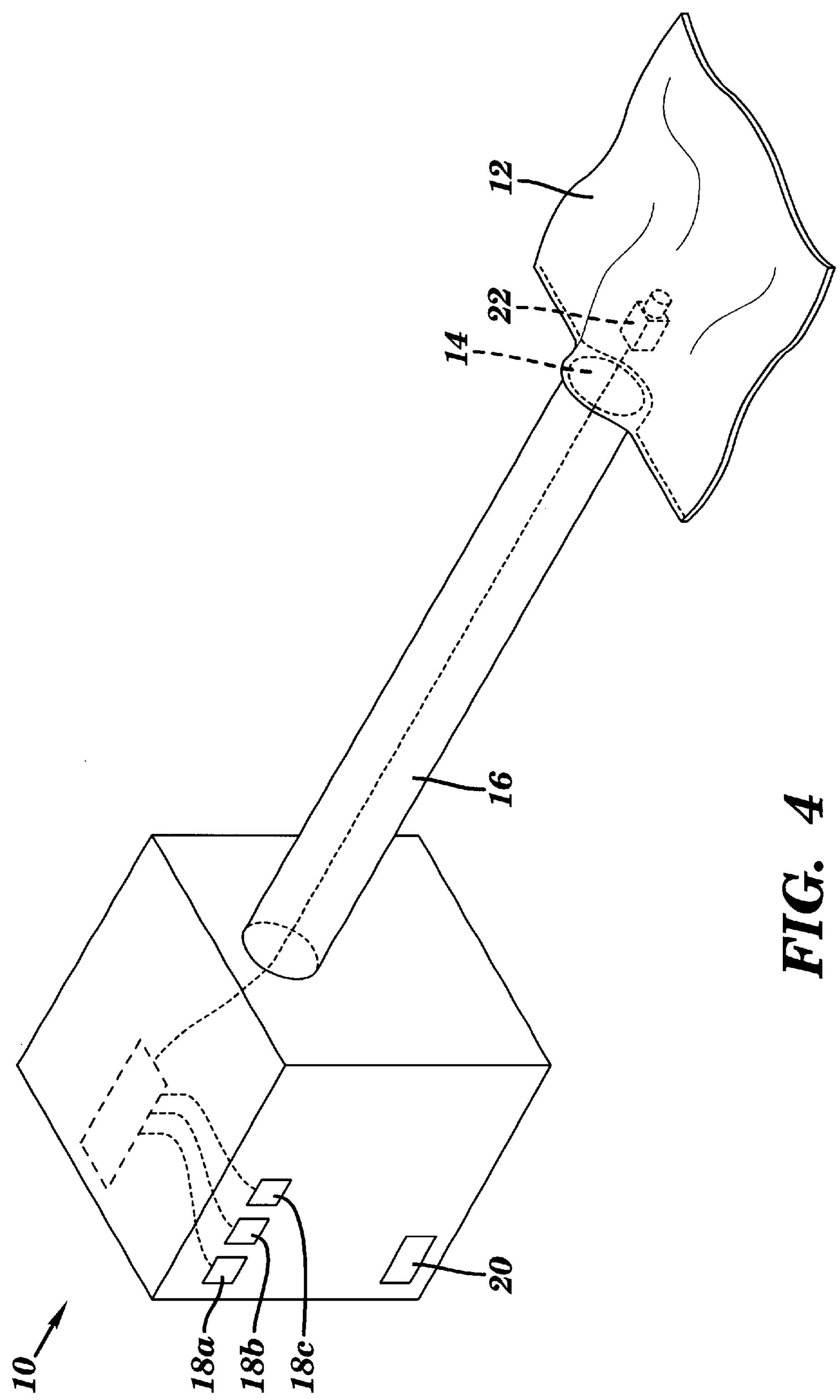

The predetermined level is measured by a pressure sensing apparatus 22. Pressure sensing apparatus 22 is a conventional pressure switch or a pressure transducer. An example of a conventional pressure sensing apparatus is, but not limited to, a Model 500 pressure switch sold by Micro Pneumatic Logic, Inc. of Fort Lauderdale, Fla. The pressure sensing apparatus 22 can be positioned within the device 10 as shown in FIG. 1, within the hose 16 as shown in FIG. 2, outside the hose 16 as shown in FIG. 3, or within the blanket 12 as shown in FIG. 4. In any position, the pressure sensing apparatus 22 is interconnected with the temperature switches 18.

If the pressure sensing apparatus 22 measures and senses the internal pressure of the medium, and the internal pressure exceeds the predetermined level, which can be any pressure level, for example, 0.3 inches of $H_2O$, then any of the temperature switches 18 can be used. If all of the temperature switches 18 can be used, then the user can select the desired temperature setting of the medium. In contrast, if the pressure sensing apparatus 22 measures the internal pressure of the medium, and the internal pressure fails to exceed the predetermined level, then the device 10 will convey the medium at a predetermined temperature setting.

The predetermined temperature setting of the medium may be one of the temperatures settings designated by switches 18, or an entirely different one (for example, no heat). In either case, the predetermined temperature is a temperature that will minimize the chances of burning, freezing, and/or damaging the skin or body hair of the patient.

Figure 5:
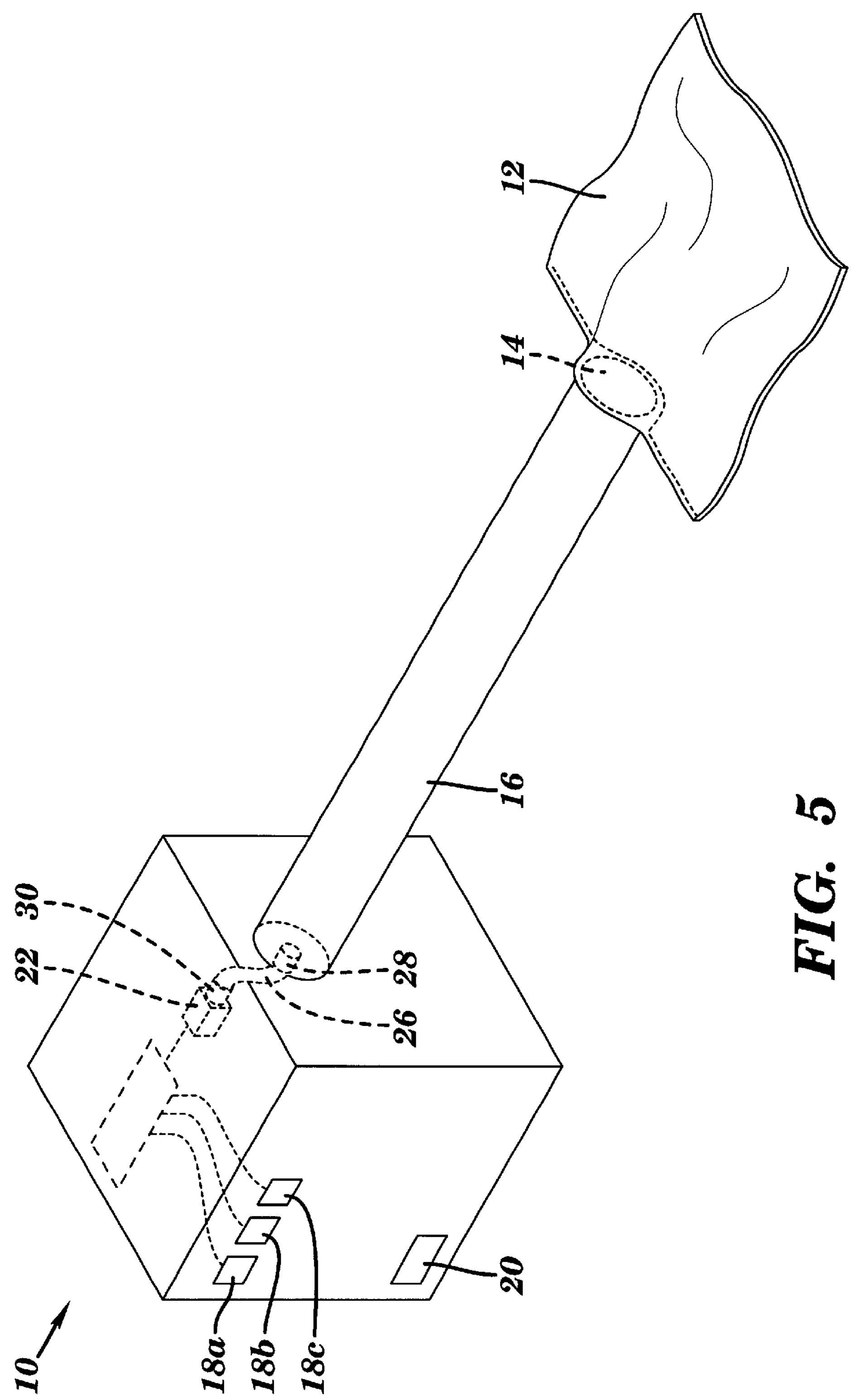
Figure 6:
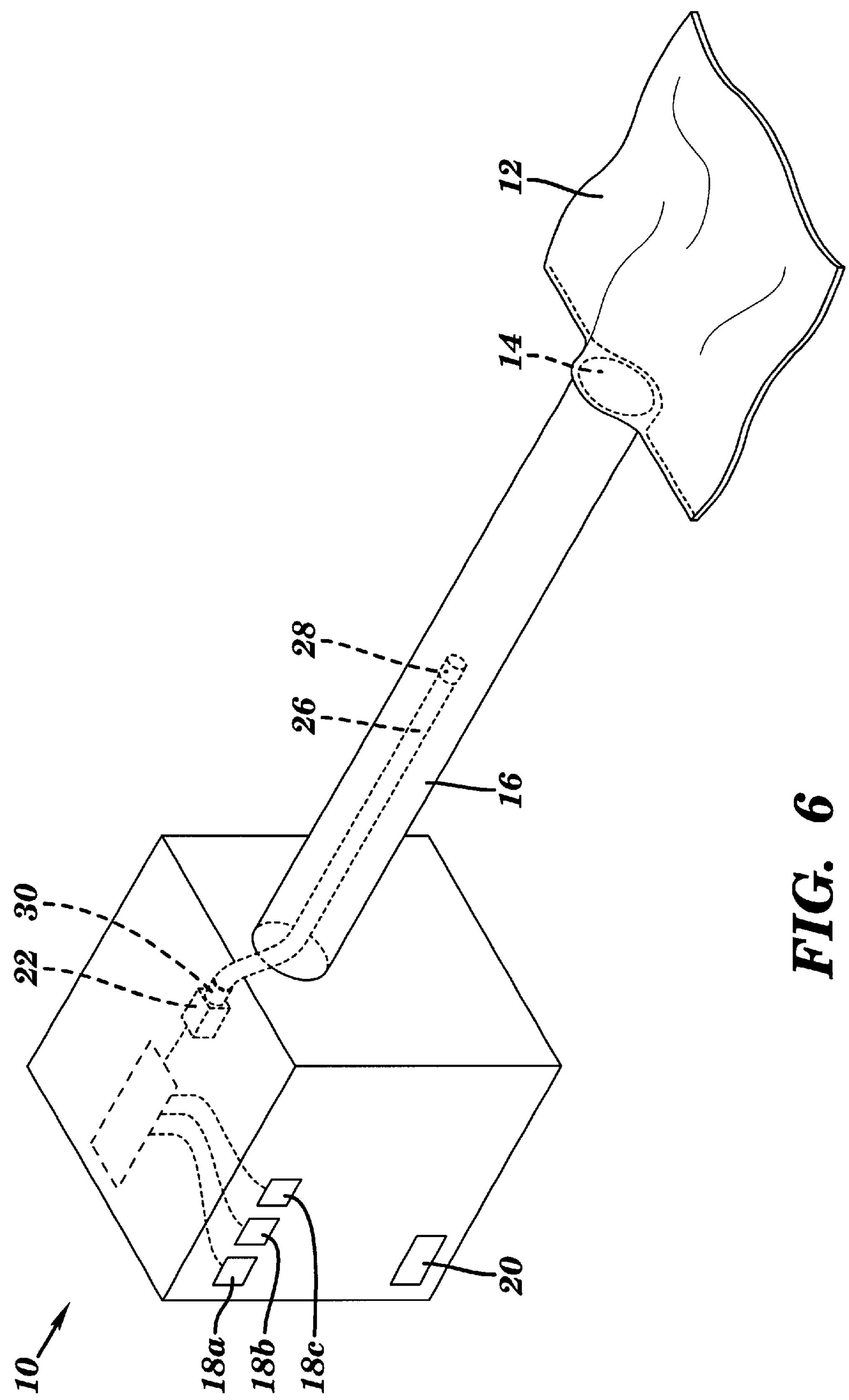
Figure 7:
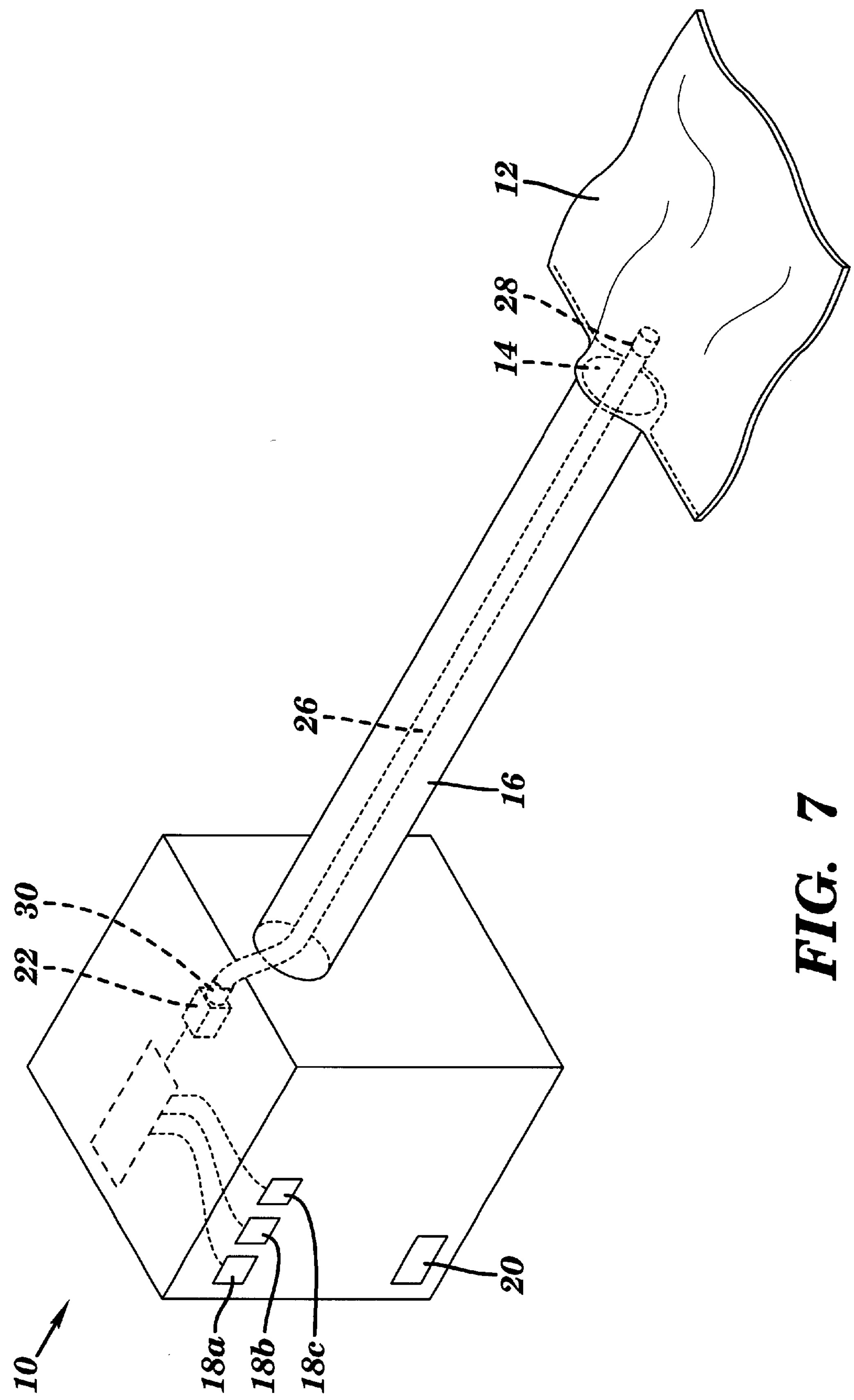

In an alternative embodiment, the pressure sensing apparatus 22 has a second conduit 26. The second conduit 26 has a distal end 28 and a proximal end 30. The proximal end 30 interconnects with the pressure sensing apparatus 22, while the distal end 28 receives the internal pressure within the blanket 12 as shown in FIG. 5, the first conduit 16 as shown in FIGS. 3 and 6, or the device 10 as shown in FIG. 7. In any embodiment, the second conduit conveys the internal pressure to the pressure sensing apparatus 22 so the pressure sensing apparatus 22 measures the internal pressure and thereby controls the switches 18.

It is intended that the above description of the preferred embodiments of the structure of the present invention and the description of its operation are but one or more enabling best mode embodiments for implementing the invention. Other modifications and variations are likely to be conceived of by those skilled in the art upon a reading of the preferred embodiments and a consideration of the appended claims and drawings. These modifications and variations still fall within the breadth and scope of the disclosure of the present invention.

We claim:

1. A method of using a device designed to interconnect with an inflatable thermia blanket through a first conduit having a proximal end and a distal end, the proximal end connects to the device and the distal end is designed to connect to the blanket, the device is designed to convey a medium into the blanket through the first conduit, the device has at least two temperature settings for controlling the temperature of the medium, an internal pressure of the medium is created when the device is operating, the method comprising the steps of:

positioning the distal end to transmit the medium to a first object;

measuring the internal pressure by a pressure sensing apparatus located in a position selected from the group consisting of within the device, between the proximal end and not contacting the distal end, and within the blanket;

if the measurement exceeds a predetermined internal pressure, then selecting any of the at least two temperature settings when the measurement exceeds a predetermined internal pressure, if the measurement is below the predetermined internal pressure then interconnecting the device to a second object having a configuration that allows the internal pressure to exceed the predetermined internal pressure in order for any of the at least two temperature settings to operate.

2. The method of claim 1 wherein the pressure sensing apparatus is positioned within the first conduit.

3. The method of claim 1 wherein the pressure sensing apparatus is positioned within the blanket.

4. The method of claim 1 wherein the pressure sensing apparatus is positioned on the exterior of the first conduit.

5. The method of claim 1 further comprising a second conduit have a second proximal end and a second distal end, the second proximal end connects to the pressure sensing apparatus, and the second distal end is located in a position selected from the group consisting of within the device, between the proximal end and not contacting the distal end, and within the blanket; and receives the internal pressure so the pressure sensing apparatus can measure the internal pressure.

6. The method of claim 1 wherein the second distal end is within the device.

7. The method of claim 1 wherein the predetermined temperature setting is one of the at least two temperature settings.

8. The method of claim 1 wherein the predetermined temperature setting is different one of the at least two temperature settings.

9. The method of claim 1 wherein the second object is a thermia blanket that properly disperses the medium.

10. A device designed to interconnect with an inflatable thermia blanket through a first conduit having a proximal end and a distal end, the proximal end connects to the device and the distal end is designed to connect to the thermia blanket, the device conveys a medium into the blanket through the first conduit, the device has at least two temperature settings for controlling the temperature of the medium, an internal pressure of the medium is created when the device is operating, the device comprising:

a pressure sensing apparatus located in a position selected from the group consisting of within the device, between the proximal end and not contacting the distal end, and within the blanket; the pressure sensing apparatus measures the internal pressure such that when the measurement exceeds a predetermined level of internal pressure then any one of the at least two temperature settings is useable, otherwise when the measurement does not exceed the predetermined level of internal pressure the device will convey the medium at a predetermined temperature setting.

11. The device of claim 10 wherein the pressure sensing apparatus is positioned within the first conduit.

12. The device of claim 10 wherein the pressure sensing apparatus is positioned on the exterior of the first conduit.

13. The device of claim 10 further comprising a second conduit have a second proximal end and a second distal end, the second proximal end connects to the pressure sensing apparatus, and the second distal end is located in a position selected from the group consisting of within the device, between the proximal end and not contacting the distal end, and within the blanket; and receives the internal pressure so the pressure sensing apparatus can measure the internal pressure.

14. The device of claim 13 wherein the second distal end is within the first conduit.

15. The device of claim 10 wherein the predetermined temperature setting is one of the at least two temperature settings.

16. The device of claim 10 wherein the predetermined temperature setting is different than any of the at least two temperature settings.

* * * * *